United States Patent [19]

Geerts et al.

[11] Patent Number: 5,658,938

[45] Date of Patent: Aug. 19, 1997

[54] SUBSTITUTED 1H-IMIDAZOLES

[75] Inventors: Jean-Pierre Geerts, Leglise; Genevieve Motte, Chastre; Edmond Differding, Louvain-la-Neuve, all of Belgium; Jean-Pierre Henichart, La Neuville, France

[73] Assignee: U C B S.A., Brussels, Belgium

[21] Appl. No.: 569,947

[22] Filed: Dec. 8, 1995

[30] Foreign Application Priority Data

Dec. 14, 1994 [GB] United Kingdom ............... 9425211

[51] Int. Cl.⁶ ...................... A61K 31/415; C07D 233/56
[52] U.S. Cl. ...................... 514/400; 514/396; 548/335.1; 548/341.1; 548/343.1; 548/345.1
[58] Field of Search ............................... 514/396, 400; 548/335.1, 341.1, 343.1, 345.1

[56] References Cited

U.S. PATENT DOCUMENTS

| | | | |
|---|---|---|---|
| 4,689,339 | 8/1987 | Karjalainen et al. | 548/345.1 |
| 4,814,343 | 3/1989 | Cossement et al. | 514/397 |
| 4,910,214 | 3/1990 | Karjalainen et al. | 514/396 |

FOREIGN PATENT DOCUMENTS

| | | |
|---|---|---|
| 0310745 | 4/1989 | European Pat. Off. |
| 2206880 | 1/1989 | United Kingdom . |

OTHER PUBLICATIONS

Amemiya et al., J. Med. Chem. vol. 35, No. 4, 21 Feb. 1992, pp. 750–755.

Primary Examiner—Patricia L. Morris
Attorney, Agent, or Firm—Wenderoth, Lind & Ponack

[57] ABSTRACT

Substituted 4-(1,2,3,4-tetrahydro-1-naphthalenyl)-1H-imidazoles and 4-(2,3-dihydro-1H-inden-1-yl)-1H-imidazoles, their optical isomers and their racemic mixtures, their salts, methods for preparing them and therapeutic compositions containing them. These compounds have the general formula

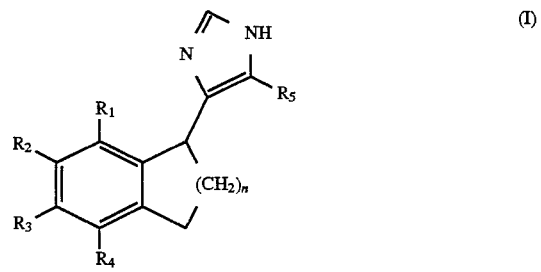

wherein
n=1 or 2,
$R_1$, $R_2$, $R_3$ and $R_4$=hydrogen, halogen, hydroxyl $C_1$–$C_4$ alkyl or $C_1$–$C_4$ alkoxy,
$R_5$= hydrogen of $C_1$–$C_4$ alkyl with the proviso that $R_1$, $R_2$, $R_3$, $R_4$ and $R_5$, cannot simultaneously be hydrogen when n is equal to 2.

These new compounds exhibit anti-ischemic and anti-hypertensive activities.

13 Claims, No Drawings

SUBSTITUTED 1H-IMIDAZOLES

The present invention relates to new substituted 4-(1,2 3,4-tetrahydro-1-naphthalenyl)-1H-imidazoles and 4-(2,3-dihydro-1H-inden-1-yl)-1H-imidazoles, and the non-toxic pharmaceutically acceptable acid addition salts thereof, as well as to processes for the preparation thereof and to the therapeutic use thereof.

It also relates to pharmaceutical compositions containing these new compounds.

K. Matsumoto et al. (203rd ACS National Meeting, Poster n° MEDI-164, San Francisco, 5–10th Apr. 1992) synthesized 4-(1,2,3,4-tetrahydro-1-methyl-1-naphthalenyl) -1H-imidazole and a derivative which is demethylated in position 1. These compounds are studied for their $\alpha_2$-adrenergic receptor agonist properties. However, this article only mentions a slight affinity towards $\alpha$-adrenergic receptors, for the methylated derivative.

U.S. Pat. No. 4,923,865 (assigned to the assignee of the present invention) describes 1-(1H-imidazol-4-yl)alkyl-benzamides which possess cardiac anti-ischemic properties and a strong presynaptic $\alpha_2$-adrenergic receptor agonist activity. These compounds also exhibit a certain diuretic activity.

Continuing research in this field, we have now synthesized new substituted 1H-imidazoles which surprisingly possess simultaneously $\alpha_2$-presynaptic agonist and $\alpha_1$-postsynaptic antagonist properties.

The compounds according to the present invention not only possess excellent cardiac anti-ischemic properties related to their presynaptic $\alpha_2$-agonist properties, but also possess $\alpha_1$-adrenergic receptor antagonist properties which give them in addition an anti-hypertensive activity due to peripheral vasodilation.

These new compounds can therefore be used, inter alia, for the prevention and the treatment of disorders induced by ischemias in general. At the cardiac level, angor is the clinical expression of an acute myocardiac ischemia, which is the result of a momentary imbalance between the myocardial oxygen demand and the oxygen supplied by the coronary circulation; this imbalance can lead in severe cases to myocardial infarction. For this reason, these compounds are especially useful for the treatment of angor and of myocardial infarction. These pathological ischemic conditions are often caused by and are the syndrome of arterial hypertension, which represents an aggravating factor since the vascular resistance opposed to the cardiac muscle increases the effort required and amplifies the imbalance between the oxygen supply and demand by the coronary circulation.

The compounds of the invention, in addition to their beneficial effects in ischemia, which are related to their $\alpha_2$-adrenergic receptor agonist properties, also possess beneficial effects related to their $\alpha_1$-adrenergic receptor antagonist properties, which are responsible for the antihypertensive effects observed. The unexpected combination of these two properties gives a new therapeutic profile to the compounds of the invention, which is particularly useful in ischemia conditions accompanied by arterial hypertension, whether the latter is the cause or the consequence of ischemia.

The compounds of the invention are thus particularly useful in the treatment of hypertensive ischemic cardiopathies, for which, most often until now, associations of medicines, such as β-blockers and nitrated derivatives or dihydropyridines and nitrated derivatives, have to be used, or, optionally, compounds or mixtures of compounds combining two complementary properties, such as labetalol ($\alpha$-antagonist and β-blocker) have to be used.

The compounds of the invention advantageously combine in a one and only molecule both postsynaptic $\alpha_1$-antagonist and presynaptic $\alpha_2$-agonist properties.

In addition to the effects on ischemia and arterial tension, the benefit of this particular combination of properties lies in the fact that, unlike β-blockers, all risk of asthma exacerbation can be avoided in sensitive subjects. The harmful effects on the lipid profile induced by β-blockers is also avoided. On the contrary, a favorable effect can be expected in this field as it has been reported in the literature for selective $\alpha_1$-antagonists.

The new compounds of the present invention are substituted 4-(1,2,3,4-tetrahydro-1-naphthalenyl)-1H-imidazoles and substituted 4-(2,3-dihydro-1H-inden-1-yl)-1H-imidazoles having the general formula

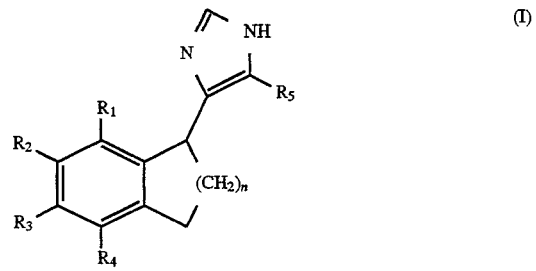

(I)

wherein
n=1 or 2, $R_1$, $R_2$, $R_3$ and $R_4$, which may be the same or different, each represent a hydrogen or halogen atom, a hydroxyl group, or an alkyl or alkoxy radical, and $R_5$ represents a hydrogen atom or an alkyl radical, with the proviso that $R_1$, $R_2$, $R_3$, $R_4$ and $R_5$ cannot simultaneously be hydrogen when n is equal to 2, the alkyl and alkoxy radicals having 1 to 4 carbon atoms, or the non-toxic pharmaceutically acceptable acid addition salts thereof.

The compounds of the present invention are 4-(2,3-dihydro-1H-inden-1-yl)-1H-imidazoles when n is equal to 1; the compounds of the present invention are 4-(1,2,3,4-tetrahydro-1-naphthalenyl)-1H-imidazoles when n is equal to 2.

The molecule contains an asymmetric carbon atom. The compounds of formula I can thus either be in the racemic form or in the form of one or the other enantiomer. These various forms also fall within the scope of the present invention.

Preferred compounds according to the invention are:
(+)-4-(1,2,3,4-tetrahydro-6-methoxy-1-naphthalenyl)-1H-imidazole,
4-(1,2,3,4-tetrahydro-5-methyl-1-naphthalenyl)-1H-imidazole,
4-(2,3-dihydro-5-methoxy-1H-inden-1-yl)-1H-imidazole,
(+)-5,6,7,8-tetrahydro-5-(1H-imidazol-4-yl)-2-naphthalenol,
4-(1,2,3,4-tetrahydro-5-methoxy-1-naphthalenyl)-1H-imidazole,
5,6,7,8-tetrahydro-5-(1H-imidazol-4-yl)-1-naphthalenol,
4-(1,2,3,4-tetrahydro-6-methyl-1-naphthalenyl)-1H-imidazole,
2,3-dihydro-1-(1H-imidazol-4-yl)-1H-indene-5-ol,
4-(1,2,3,4-tetrahydro-8-methoxy-1-naphthalenyl)-1H-imidazole, 4-(1,2,3,4-tetrahydro-6,7-dimethoxy-1-naphthalenyl)-
1H-imidazole, 5,6,7,8-tetrahydro-5-(1H-imidazol-4-yl)
-2,3-naphthalenediol.

The present invention also relates to the non-toxic pharmaceutically acceptable acid addition salts of the substituted 4-(1,2,3,4-tetrahydro-1-naphthalenyl)-1H-imidazoles and 4-(2,3-dihydro-1H-inden-1-yl)-1H-imidazoles of formula I. Examples of pharmaceutically acceptable acids that may be mentioned include inorganic acids such as hydrochloric acid, hydrobromic acid, sulfuric acid, nitric acid, phosphoric acid, and the like, and organic acids such as acetic acid, citric acid, tartaric acid, benzoic acid, salicylic acid and maleic acid, and the like.

The general method for preparing the 4-(1,2,3,4-tetrahydro-1-naphthalenyl)-1H-imidazoles of formula

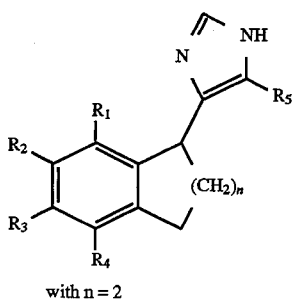

with n = 2 in which $R_1$, $R_2$, $R_3$ and $R_4$ each represent a hydrogen or halogen atom, an alkyl or alkoxy radical, the alkyl and alkoxy radicals having 1 to 4 carbon atoms, comprises cyclizing a 4-phenyl-1-(1-triphenylmethyl-1H-imidazol-4-yl)-1-butanol of the formula

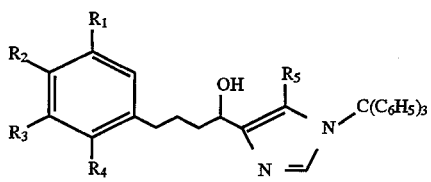

wherein $R_1$, $R_2$, $R_3$ and $R_4$ have the meaning given above and $R_5$ represents a hydrogen atom or an alkyl radical having 1 to 4 carbon atoms.

This cyclization reaction is generally carried out in the presence of an organic acid such as formic acid (which acts simultaneously as a solvent) at the boiling point of the solvent.

The method for preparing substituted 4-(2,3-dihydro-1H-inden-1-yl)-1H-imidazoles of the formula

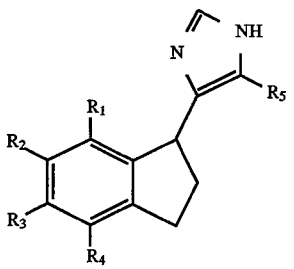

with n = 1 in which $R_1$, $R_2$, $R_3$ and R4 each represent a hydrogen or halogen atom, an alkyl or alkoxy radical, the alkyl and alkoxy radicals having 1 to 4 carbon atoms, comprises the catalytic hydrogenation by molecular hydrogen of a 4-(1H-inden-3-yl)-1H-imidazole of the formula

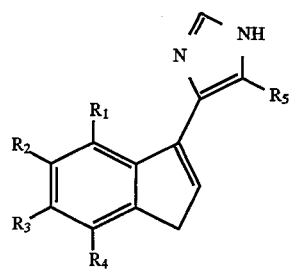

wherein $R_1$, $R_2$, $R_3$ and $R_4$ have the meaning given above and $R_5$ represents a hydrogen atom or an alkyl radical having 1 to 4 carbon atoms.

This reaction is generally carried out in an autoclave, under a hydrogen pressure of 1 to 10 kg, in a solvent, in the presence of a catalyst such as palladium on carbon, at a temperature generally comprised between 20° and 80° C.

In yet another embodiment, directed to the preparation of substituted 1H-imidazoles of formula I in which at least one of $R_1$, $R_2$, $R_3$ and $R_4$ represents a hydroxyl group, selective dealkylation of one or several alkoxy radicals having 1 to 4 carbon atoms in the substituted 1H-imidazole of the formula

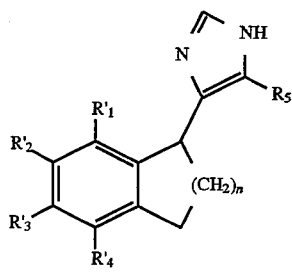

(I) with $R_1$, $R_2$, $R_3$ or
$R_4$ = alkoxy with $C_1$–$C_4$ wherein n=1 or 2 and $R'_1$, $R'_2$, $R'_3$ and $R'_4$ represent a hydrogen or halogen atom, an alkyl or alkoxy radical, the alkyl and alkoxy radicals having 1 to 4 carbon atoms, at least one of the symbols $R'_1$, $R'_2$, $R'_3$ and $R'_4$ being an alkoxy radical and $R_5$ having the meaning given above, is performed in solution in a solvent, by treating the compound of formula IV with hydrobromic acid or boron tribromide ($BBr_3$).

The non-toxic, pharmaceutically acceptable acid addition salts can be prepared from the 1H-imidazoles of formula I by per se known methods.

The compounds of formula I which are in the form of a racemic mixture, can be separated into their enantiomers by conventional methods, either by fractional crystallization of the diastereoisomeric salts obtained by addition of an optically active acid to the racemic mixture, or by chromatography of the racemic mixture on a chiral support such as, for example, a silica on which bovine serum albumin (BSA) is covalently grafted or a phase containing α-glycoprotein or β-cyclodextrin. Several successive passes through the chiral chromatographic column may sometimes be necessary in order to improve the separation of the enantiomers.

The starting 4-phenyl-1-(1-triphenylmethyl-1H-imidazol-4-yl)-1-butanols of formula II can be prepared from suitably substituted brominated derivatives of formula V, and from 1-triphenylmethyl-1H-imidazole-4-carboxaldehydes of formula VI, by means of a Grignard reaction in the presence of magnesium turnings, according to the equation

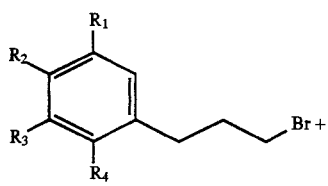

(V)

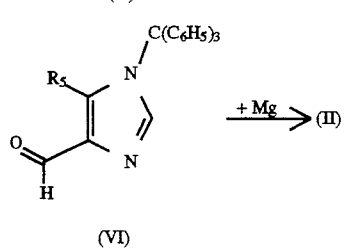

(VI)

in these formulae, $R_1$, $R_2$, $R_3$ and $R_4$ each represent a hydrogen or halogen atom, an alky or alkoxy radical, the alkyl and alkoxy radicals having 1 to 4 carbon atoms and $R_5$ having the meaning given above.

The brominated derivatives of formula V used as starting materials are known or commercial compounds.

The 1-triphenylmethyl-1H-imidazole-4-carboxaldehydes of formula VI may be obtained, in general, by oxidation of the corresponding 1H-imidazole-4-methanols, using activated $MnO_2$, according to the method described by J. L. Kelley, C. A. Miller and E. W. McLean (J. Med. Chem. 20, (1977), 721–723).

The starting 4-(1H-inden-3-yl)-1H-imidazoles of formula III may be prepared by a multi-step process:

(1) Claisen-Schmidt condensation between a suitable benzaldehyde of formula VII and a 1-(1-triphenylmethyl-1H-imidazol-4-yl)-1-ethanone of formula VIII in order to obtain a 3-phenyl-1-(1-triphenylmethyl-1H-imidazol-4-yl)-2-propen-1-one of formula IX according to the equation

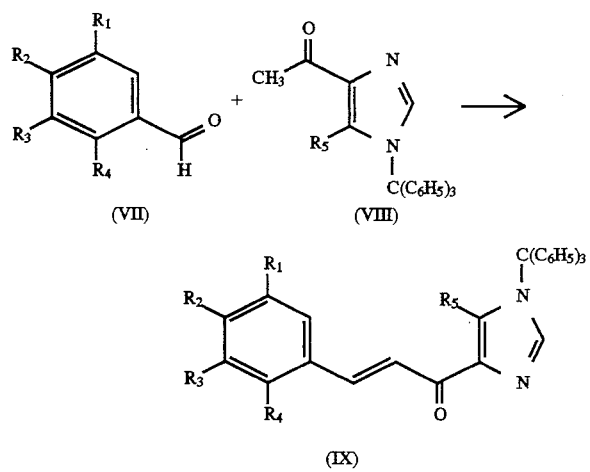

(2) hydrogenation under a hydrogen pressure of 4 kg in the presence of platinum oxide of the 3-phenyl-1-(1-triphenylmethyl-1H-imidazol-4-yl)-2-propen-1-one of formula IX into the corresponding 1-propanone derivative of formula X, according to the equation:

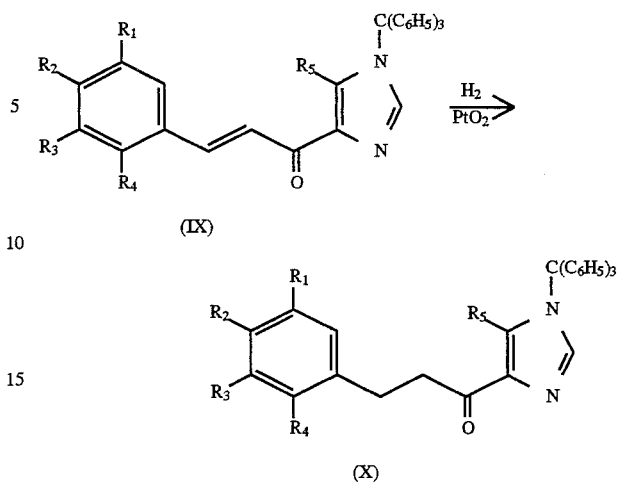

(3) followed by detritylation by heating in formic acid of the compound of formula X into a 1-(1H-imidazol-4-yl)-3-phenyl-1-propanone of formula

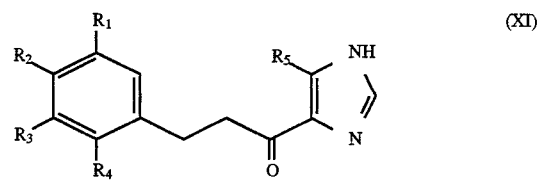

(4) cyclization of the compound of formula XI in an acid medium to form the 4-(1H-inden-3-yl)-1H-imidazole of formula III

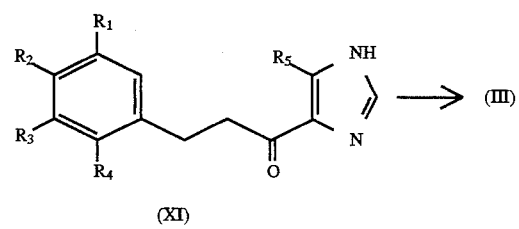

in these formulae, $R_1$, $R_2$, $R_3$ and $R_4$ each represent a hydrogen or halogen atom, an alkyl or alkoxy radical, the alkyl and alkoxy radicals having 1 to 4 carbon atoms and $R_5$ having the meaning given above.

The 1-(1-triphenylmethyl-1H-imidazol-4-yl)-1-ethanones of formula VIII used as starting material, can be obtained by oxidizing α-methyl-1-triphenylmethyl-1H-imidazole-4-methanols with $MnO_2$ using the method described by J. L. Kelley et al. (J. Med. Chem. 20, (1977), 721–723; also in U.S. Pat. No. 4,814,343, col. 18).

As already mentioned above, the substituted 1H-imidazoles of formula I, as well as their non-toxic pharmaceutically acceptable acid addition salts, possess valuable pharmacological properties; in particular, it has been found that they have excellent cardiac anti-ischemic properties associated with useful anti-hypertensive properties.

The pharmacological tests presented below illustrate these various properties.

The following compounds according to the present invention have been subjected to in vitro and in vivo pharmacological tests:

(+)-4-(1,2,3,4-tetrahydro-6-methoxy-1-naphthalenyl)-1H-imidazole (Compound A).

4-(1,2,3,4-tetrahydro-5-methyl-1-naphthalenyl)-1H-imidazole (Compound B), 4-(2,3-dihydro-5-methoxy-1H-inden-1-yl)-1H-imidazole (Compound C), (+)-5,6,7,8-tetrahydro-5-(1H-imidazol-4-yl)-2-naphthalenol (Compound D), 4-(1,2,3,4-tetrahydro-5-methoxy-1-naphthalenyl)-1H-imidazole (Compound E), 5,6,7,8-tetrahydro-5-(1H-imidazol-4-yl)-1-naphthalenol hydrochloride (Compound F), 4-(1,2,3,4-tetrahydro-6-methyl-1-naphthalenyl)-1H-imidazole (Compound G), 2,3-dihydro-1-(1H-imidazol-4-yl)-1H-indene-5-ol hydrochloride (Compound H), 4-(1,2,3,4-tetrahydro-8-methoxy-1-naphthalenyl)-1H-imidazole (Compound I), 4-(1,2,3,4-tetrahydro-6,7-dimethoxy-1-naphthalenyl)-1H-imidazole (Compound J), and 5,6,7,8-tetrahydro-5-(1H-imidazol-4-yl)-2,3-naphthalenediol hydrochloride (Compound K).

Anti-ischemic and anti-hypertensive activity.

The cardiac anti-ischemic activity of compounds manifests itself by their capacity to oppose the elevation of the T wave of the electrocardiogram, induced by a coronary occlusion in the rat. Continuous monitoring of the arterial pressure also enables to reveal the anti-hypertensive effects. The animal used for the test is a male albino rat of the Sprague-Dawley strain, weighing 220 to 280 g. On the day of the experiment, the animal is anesthetized by intraperitoneal administration of pentobarbital (60 mg/kg), then placed under endotracheal intubation. A ligature system is fitted around the descending left anterior coronary artery according to the procedure of Johnston et el. (Can. J. Physiol. Pharmacol., 61 (1983), 1340–1353). After closing the thorax, three electrodes are arranged on the body of the animal ("V4" thoracic derivation), in order to continuously record the shape of the electrocardiogram signal (in particular the T wave). Catheters are introduced into the right carotid artery and the right jugular vein to measure the arterial pressure and to administer intravenously the compound tested or the vehicle solution. Four 45 second coronary occlusions are performed, separated by episodes of reperfusion of 30, 35 and 30 minutes respectively. The compound to be studied or the vehicle are administered intravenously in bolus, 30 minutes before occlusion 3. The T electrocardiographic signal and the arterial pressure are continuously measured during the entire experiment.

The effects of the compounds according to the invention are quantified by comparing the amplitude of the elevation of the T wave at occlusions 3 and 4 (that is 30 minutes and 60 minutes after administration) with its value at occlusion 2 (that is before administration). The results are summarized in the following Table I in which:

the first column indicates the compound tested;

the second column indicates the dose of compound administered, expressed in mole/kg;

the third and the fourth columns indicate the anti-ischemic effect caused by administering the compound tested. The anti-ischemic effect represents the reduction in the elevation of the T wave caused by coronary occlusions 3 and 4, expressed in % with respect to occlusion 2, before administration of the compound ($\Delta T3$ and $\Delta T4$ respectively);

the fifth and sixth columns indicate the anti-hypertensive effect caused by administration of the compound tested.

The anti-hypertensive effect is expressed as the maximum lowering of arterial pressure, measured a) between 5 and 30 minutes, and b) between 30 and 60 minutes after intravenous injection of the compound tested ($\Delta Pa$ and $\Delta Pb$ respectively). This lowering is expressed in % with respect to the value measured before injection.

The following products are used as reference substances:

oxymetazoline: 3-[(4,5-dihydro-1H-imidazol-2-yl)methyl]-6-(1,1-dimethylethyl)-2,4-dimethylphenol, a presynaptic $\alpha_2$-agonist;

mivazerol: 2-hydroxy-3-[(1H-imidazol-4-yl)methyl] benzamide hydrochloride, a presynaptic $\alpha_2$-agonist (U.S. Pat. No. 4,923,865);

prazosin: 1-(4-amino-6,7-dimethoxy-2-quinazolinyl)-4-(2-furanylcarbonyl)piperazine, a postsynaptic $\alpha_1$-antagonist, and;

propranolol: 1-[(1-methylethyl)amino]-3-(1-naphthalenyloxy)-2-propanol, a conventional anti-hypertensive agent and β-blocker.

TABLE I

Anti-ischemic and anti-hypertensive activity

| Compound | Dose (mole/kg) | $\Delta T3$ (%) | $\Delta T4$ (%) | $\Delta Pa$ (%) | $\Delta Pb$ (%) |
|---|---|---|---|---|---|
| A | $3.2 \times 10^{-7}$ | −80 | −33 | −32 | −28 |
| B | $3.2 \times 10^{-8}$ | −48 | −29 | −33 | −16 |
| C | $3.2 \times 10^{-7}$ | −52 | −66 | −44 | −43 |
| D | $1.0 \times 10^{-7}$ | −50 | −31 | −30 | −17 |
| E | $1.0 \times 10^{-7}$ | −31 | −13 | −45 | −20 |
| F | $3.2 \times 10^{-7}$ | −64 | −59 | −32 | −36 |
| G | $3.2 \times 10^{-7}$ | −24 | −16 | −22 | −14 |
| H | $3.2 \times 10^{-7}$ | −48 | −55 | −23 | −19 |
| I | $1.0 \times 10^{-6}$ | −37 | −57 | −26 | −16 |
| J | $1.0 \times 10^{-6}$ | −31 | −29 | −23 | −16 |
| K | $3.2 \times 10^{-7}$ | −49 | −47 | −29 | −41 |
| Oxymetazoline | $3.2 \times 10^{-8}$ | −45 | −38 | 0 | 0 |
| Mivazerol | $3.2 \times 10^{-8}$ | −34 | −22 | −1 | −6 |
| Prazosin | $3.2 \times 10^{-7}$ | NS | NS | −34 | −31 |
| Propranolol | $3.2 \times 10^{-6}$ | −21 | −30 | 7 | 5 |

NS: results not significant ($p > 0.05$)

With the exception of the values for the lowering in elevation of the T wave measured for prazosin, all the values given in Table I are statistically significant ($p<0.05$). This Table shows that the compounds of the invention are anti-ischemic ($-13\% \leq \Delta T \leq -80\%$) at doses of between $10^{-6}$ and $3.2 \times 10^{-8}$ mole/kg. This property is accompanied by a lowering of arterial pressure ($-14\% \leq \Delta P \leq -46\%$) at the same doses.

The reference substances cited also show the absence of an effect on arterial pressure ($0 \leq \Delta P \leq -6\%$) for typical presynaptic $\alpha_2$-agonists such as oxymetazoline or mivazerol and the absence of a significant anti-ischemic effect for the anti-hypertensive drug of the $\alpha_1$-antagonist type such as prazosin. Finally, it will be noted that products according to the invention are more active than propranolol (a conventional drug used in human clinical practice for cardiac ischemic therapy), from the point of view of the anti-ischemic activity as well as from the point of view of the anti-hypertensive effect.

2. Stimulation of the guinea-pig ileum.

Longitudinal muscle strips attached to an isometric strain gauge are suspended in Tyrode's solution and are stretched under a tension of 1 g (G. M. Drew, Brit. J. Pharmacol. 64, (1978), 293–300; M. Andréjak et al., Naunyn-Schmiedeberg's Arch. Pharmacol. 314, (1980), 83–87).

Electrical stimulation of the parasympathetic nerves associated with the ileum fragments causes a contraction of the muscle. This contraction is reduced in the presence of a presynaptic $\alpha_2$-agonist and the magnitude by which the contraction is reduced depends on the concentration of the agonist used. This effect is antagonised by the simultaneous presence of an $\alpha_2$-antagonist such as alpha-yohimbine. The compounds to be studied have been tested at increasing concentrations ranging from $10^{-10}$ and $10^{-4}$ mole/l.

The $IC_{30}$ concentration (in mole/l) that reduces by 30% the intensity of the contraction of the muscle is determined.

Table II gives the $IC_{30}$ concentrations (in mole/l) obtained for the compounds of the invention.

TABLE II

Inhibition of the contraction of the guinea pig ileum

| Compound | $IC_{30}$ (in mole/l) |
|---|---|
| A | $3 \times 10^{-8}$ |
| B | $8.8 \times 10^{-10}$ |
| C | $3.2 \times 10^{-8}$ |
| D | $1.8 \times 10^{-9}$ |
| E | $1.7 \times 10^{-9}$ |
| F | $3.7 \times 10^{-9}$ |
| G | $3 \times 10^{-8}$ |
| H | $3.6 \times 10^{-8}$ |
| I | $8 \times 10^{-6}$ |
| J | $1.3 \times 10^{-7}$ |
| K | $1.6 \times 10^{-8}$ |
| Oxymetazoline | $1.2 \times 10^{-8}$ |

In the presence of alpha-yohimbine at a concentration of $10^{-6}$ mole/l, the concentration of the compounds necessary to reduce the intensity of contraction of the muscle by 30% is higher and becomes greater than $10^{-6}$ mole/l, which confirms that the compounds of the invention really act at the level of the presynaptic $\alpha_2$-adrenergic receptors. Table II also shows that the compounds of the invention are at least as active as, if not more active than, a typical presynaptic $\alpha_2$-agonist such as oxymetazoline.

3. Post-synaptic $\alpha_1$-antagonist activity.

A non selective $\alpha$-agonist substance such as norepinephrine induces a sustained contraction of the isolated aorta of the rat (J. M. Van Rossum Arch. Int. Pharmacodyn. 143, (1963), 299–330). This contraction can be inhibited by $\alpha_1$-adrenergic blocking substances such as prazosin. In this test, a control contraction is carried out with norepinephrine at $3.2 \times 10^{-8}$ mole/l. After washing and stabilizing the preparation, the compound to be tested is added to the bath. Norepinephrine is added 5 minutes after the compound tested, and inhibition of the contraction induced by norepinephrine is measured. Next, inhibition of the contraction induced by norepinephrine is evaluated a second and third time in the presence of increasing concentrations of the compound tested.

Table III below gives the concentration in mole per liter which causes 30% inhibition of the contraction induced by norepinephrine.

TABLE III

Postsynaptic $\alpha_1$-antagonist activity

| Compound | $ED_{30}$ (mole/l) |
|---|---|
| A | $2.1 \times 10^{-8}$ |
| B | $3.3 \times 10^{-8}$ |
| C | $1.0 \times 10^{-7}$ |
| D | $4.2 \times 10^{-7}$ |
| E | $4.6 \times 10^{-7}$ |
| F | $2.3 \times 10^{-7}$ |

TABLE III-continued

Postsynaptic $\alpha_1$-antagonist activity

| Compound | $ED_{30}$ (mole/l) |
|---|---|
| G | $7.2 \times 10^{-8}$ |
| H | $2.1 \times 10^{-7}$ |
| I | $1.8 \times 10^{-6}$ |
| J | $2.9 \times 10^{-6}$ |
| Prazosin | $2.3 \times 10^{-10}$ |

Although less active than prazosin, which, as stated before, has no anti-ischemic effect, the compounds of the invention nevertheless exhibit $\alpha_1$-antagonist activities, typically at concentrations in the order of µmoles/l or less. These activities and the presynaptic $\alpha_2$-agonist properties explain the simultaneous anti-ischemic and anti-hypertensive properties of the compounds of the invention.

4. Toxicity

The toxicity of the compounds of the invention has been determined in male NMRI mice by means of Irwin's test (S. Irwin, Psychopharmacologia (Berl.), 13, (1968), 222–257).

Progressive doses of the product studied are administered intraperitoneally to groups of three mice until a lethal dose is reached (dose causing the death of two out of three animals in 48 hours). Table IV below gives the lethal dose observed for the compounds of the invention. It follows from this Table that the compounds of the invention are not very toxic.

TABLE IV

Toxicity

| Compound | Lethal dose (in mg/kg) |
|---|---|
| A | 228.3 |
| B | >67.9 |
| C | 214.3 |
| D | >68.6 |
| E | 127.8 |
| F | 214.3 |
| G | 118.9 |
| H | 236.7 |
| I | 228.3 |
| J | 258.3 |
| K | >85.4 |

The pharmaceutical compositions containing the compounds according to the present invention may be administered orally, parenterally or rectally.

The pharmaceutical compositions which can be used for oral administration may be solid or liquid, for example in the form of tablets (coated or uncoated), pills, dragees, gelatine capsules, solutions, syrups, and the like.

Similarly, the compositions which can be used for parenteral administration are the pharmaceutical compositions known for this mode of administration, for example aqueous or oily solutions, suspensions or emulsions. For rectal administration, the compositions containing the compounds of the invention are generally used in the form of suppositories.

The pharmaceutical forms such as injectable solutions, injectable suspensions, tablets, drops, suppositories and the like are prepared by the methods currently used by pharmacists.

The compounds of the invention are mixed with a solid or liquid, non-toxic, pharmaceutically acceptable carrier, and optionally with a dispersing agent, a disintegrating agent, a stabilizing agent and the like. If desired, sweetening and coloring agents and the like may also be added.

The percentage of active compound in the pharmaceutical compositions may vary within very wide limits, according to the patient and the mode of administration, and in particular according to the frequency of administration.

As far as the daily posology is concerned, it may vary within a very wide range of dosage units depending on the mode of administration. For example, it can be from 2 to 250 µg of active compound once or twice a day by intravenous injection, or again from 20 µg to 5 mg of active compound once or twice a day by oral administration.

By way of non-limiting examples of compositions containing a compound of the invention, there are given below:

a) an example of a sterile solution for intravenous administration

| | |
|---|---|
| Active compound | 0.25 mg |
| Sodium acetate | 19.15 mg |
| Acetic acid | 3.59 mg |
| Sodium chloride | 81.0 mg |
| Sterile water | ad 10 ml |
| (to be kept in a 10 ml brown ampule, after sterile filtration of the solution). | | b) an example of a formula for a tablet:

| | |
|---|---|
| Active compound | 0.5 mg |
| Corn starch | 38 mg |
| Lactose | 63 mg |
| Magnesium stearate | 1.2 mg |
| Polyvinylpyrrolidone | 2.5 mg |

The following non-limiting examples are given for the purpose of illustrating the preparation of the substituted 1H-imidazoles according to the invention as well as the preparation of their intermediates.

EXAMPLE 1

Preparation of 4-(1,2,3,4-tetrahydro-1-naphthalenyl)-1H-imidazoles of formula I (n=2; $R_1$, $R_2$, $R_3$ and $R_4$=H, halogen or an alkyl or alkoxy radical with $C_1$–$C_4$; and $R_5$=H or alkyl with $C_1$–$C_4$).

1.1 Preparation of the starting brominated derivatives of formula V.

1.1.a 1-(3-bromopropyl)-2-methylbenzene.

This compound is prepared according to the method described by R. Durand-Dran in Ann. Chim. (Paris), 4 (1959), 45–86.

1.1.b 1-(3-bromopropyl)-3-methylbenzene.

This compound is prepared according to the method described by M. T. Bogert et al., in J. Am. Chem. Soc., 56 (1934), 959–963.

1.1.c 1-(3-bromopropyl)-3-chlorobenzene.

This compound is prepared according to the method described by H. König et al. in Chem. Ber., 92 (1959), 429–433.

1.1.d 1-(3-bromopropyl)-3-(1-methylethoxy)benzene.
1.1.e 1-(3-bromopropyl)-2,3-dimethoxybenzene.
1.1.f 1-(3-bromopropyl)-3,4-dimethoxybenzene.
1.1.g 1-(3-bromopropyl)-3-methoxybenzene.
1.1.h 1-(3-bromopropyl)-2-methoxybenzene.
1.1.j 1-(3-bromopropyl)-2-chloro-5-methoxybenzene.

Compounds 1.1.d, 1.1.e, 1.1.f, 1.1.g, 1.1.h and 1.1.j are prepared according to the method described by T. Horaguchi et al., in J. Het. Chem., 26 (1989), 365–369.

1.2 Preparation of the starting 1-triphenylmethyl-1H-imidazole-4-carboxaldehydes of formula VI.

1.2.a 1-triphenylmethyl-1H-imidazole-4-carboxaldehyde.

This compound is prepared according to the method described by J. L. Kelley et al., in J. Med. Chem., 20 (1977), 721–723.

1.2.b 5-methyl-1-triphenylmethyl-1H-imidazole-4-carboxaldehyde.

This compound is prepared according to the method described in Example 1.B.3.c of U.S. Pat. No. 4,923,865.

1.3 Preparation of the 4-phenyl-1-(1-triphenylmethyl-1H-imidazol-4-yl)-1-butanols of formula II.

These compounds are prepared according to the following procedure: a solution containing 0.235 mole of a brominated derivative prepared in Example 1.1 in 140 ml of dry diethyl ether is prepared. 0.25 mole of magnesium turnings, 140 ml of diethyl ether dried over a sodium/lead alloy, a crystal of iodine and about 14 ml (10%) of the solution of the brominated derivative prepared above, are introduced, under nitrogen, into a 4 liter 4-necked round-bottomed flask fitted with a mechanical stirrer, a thermometer, a reflux condenser and a constant pressure dropping funnel. The mixture is heated to reflux temperature until the reaction starts, then the remaining solution of the brominated derivative (90%) is added progressively and at a rate such that the mixture is kept at reflux temperature. The mixture is maintained for an extra hour at reflux temperature, it is then cooled to room temperature and a solution of 0.23 mole of a 1-triphenylmethyl-1H-imidazole-4-carboxaldehyde prepared in Example 1.2 in 1.25 liter of dry tetrahydrofuran is added dropwise. The reaction mixture is maintained at room temperature for 1 to 4 hours whilst the progress of the reaction is followed by HPLC chromatography. When the reaction is considered to be over, the reaction mixture is cooled in an ice bath, and 600 ml of a saturated aqueous solution of ammonium chloride is added dropwise. The mixture is stirred at room temperature for half an hour and is then decanted. The aqueous phase is washed three times with 250 ml of diethyl ether and the organic phases are gathered together and then dried over sodium sulfate. The solvent is evaporated and the oil thus obtained is purified by preparative HPLC chromatography (stationary phase: 15 to 40 µm silica; eluent: 98:2 (v/v) mixture of dichloromethane-methanol).

1.3.a 4-(2-methylphenyl)-1-(1-triphenylmethyl-1H-imidazol-4-yl)-1-butanol.

This compound is obtained from the starting compounds prepared in Examples 1.1.a and 1.2.a. The 4-(2-methylphenyl)-1-(1-triphenylmethyl-1H-imidazol-4-yl)-1-butanol obtained is recrystallized from ethyl acetate.

Yield: 65%
M. Pt.: 125.1° C.
Analysis for $C_{33}H_{32}N_2O$ in %:

| | | | | | | |
|---|---|---|---|---|---|---|
| Calculated: | C | 83.86 | H | 6.83 | N | 5.93 |
| Found: | | 83.68 | | 6.91 | | 5.99 |

1.3.b 4-(3-methylphenyl)-1-(1-triphenylmethyl-1H-imidazol-4-yl)-1-butanol.

This compound is obtained from the starting compounds prepared in Examples 1.1.b and 1.2.a. The 4-(3-methylphenyl)-1-(1-triphenylmethyl-1H-imidazol-4-yl)-1-butanol obtained is recrystallized from ethyl acetate.

Yield: 53%
M. Pt.: 105.6° C.

Analysis for $C_{33}H_{32}N_2O$ in %:

| Calculated: | C | 83.86 | H | 6.83 | N | 5.93 |
|---|---|---|---|---|---|---|
| Found: | | 84.00 | | 7.07 | | 6.08 |

1.3.c 4-(3-chlorophenyl)-1-(1-triphenylmethyl-1H-imidazol-4-yl)-1-butanol.

This compound is obtained from the starting compounds prepared in Examples 1.1.c and 1.2.a. The 4-(3-chlorophenyl)-1-(1-triphenylmethyl-1H-imidazol-4-yl)-1-butanol obtained is recrystallized from ethyl acetate.
Yield: 45%
M. Pt.: 127.6° C.
Analysis for $C_{32}H_{29}C_1N_2O$ in %:

| Calculated: | C | 77.96 | H | 5.92 | N | 5.68 |
|---|---|---|---|---|---|---|
| Found: | | 78.08 | | 6.02 | | 5.46 |

1.3.d 4-(3-(1-methylethoxy)phenyl-1-(1-triphenylmethyl-1H-imidazol-4-yl)-1-butanol.

This compound is obtained from the starting compounds prepared in Examples 1.1.d and 1.2.a. The product is used as such in the following step (Example 1.4.d).
Yield:=25%
Mass spectrum: 516 ($M^+$), 498 ($M^+$- $H_2O$), 273 (triphenylmethyl cation), 243 ($M^+$-triphenylmethyl cation).

1.3e 4-(2,3-dimethoxyphenyl)-1-(1-triphenylmethyl-1H-imidazol-4-yl)1-butanol.

This compound is obtained from the starting compounds prepared in Examples 1.1.e and 1.2.a. The 4-(2,3-dimethoxyphenyl)-1-(1-triphenylmethyl-1H-imidazol-4-yl)-1-butanol obtained is recrystallized from diethyl ether.
Yield: 32.4%
M.Pt.: 95°–99° C.
Analysis for $C_{34}H_{34}N_2O_3$ in %:

| Calculated: | C | 78.76 | H | 6.56 | N | 5.40 |
|---|---|---|---|---|---|---|
| Found: | | 78.47 | | 6.58 | | 5.47 |

1.3.f 4-(3,4-dimethoxyphenyl)-1-(1-triphenylmethyl-1H-imidazol-4-yl)-1-butanol.

This compound is obtained from the starting compounds prepared in Examples 1.1.f and 1.2.a. The 4-(3,4-dimethoxyphenyl)-1-(1-triphenylmethyl-1H-imidazol-4-yl)-1-butanol obtained is recrystallized from ethyl acetate.
Yield: 25.5%
M.Pt.: 145°–146° C.
Analysis for $C_{34}H_{34}N_2O_3$ in %:

| Calculated: | C | 78.73 | H | 6.60 | N | 5.40 |
|---|---|---|---|---|---|---|
| Found: | | 78.98 | | 6.70 | | 5.40 |

1.3.g 4-(3-methoxyphenyl)-1-(1-triphenymethyl-1H-imidazol-4-yl)-1-butanol.

This compound is obtained from the starting compounds prepared in Examples 1.1.g and 1.2.a. The 4-(3-methoxyphenyl)-1-(1-triphenylmethyl-1H-imidazol-4-yl)-1-butanol obtained is recrystallized from ethylacetate.
Yield: 42.4%
M.Pt.: 105°–112° C.

Analysis for $C_{33}H_{32}N_2O_2$ in %:

| Calculated: | C | 81.15 | H | 6.56 | N | 5.74 |
|---|---|---|---|---|---|---|
| Found: | | 80.55 | | 6.65 | | 5.60 |

1.3.h 4-(2-methoxyphenyl)-1-(1-triphenylmethyl-1H-imidazol-4-yl)-1-butanol.

This compound is obtained from the starting compounds prepared in Examples 1.1.h and 1.2.a. The 4-(2-methoxyphenyl)-1-(1-triphenylmethyl-1-H-imidazol-4-yl)-1-butanol obtained is recrystallized from toluene.
Yield: 20%
M.Pt.: 161° C.
Analysis for $C_{33}H_{32}N_2O_2$ in %:

| Calculated: | C | 81.11 | H | 6.60 | N | 5.73 |
|---|---|---|---|---|---|---|
| Found: | | 81.40 | | 6.62 | | 5.78 |

1.3.i 4-(3-methoxyphenyl)-1-(5-methyl-1-triphenylmethyl-1H-imidazol-4-yl)-1-butanol.

This compound is obtained from the starting compounds prepared in Examples 1.1.g and 1.2.b. The 4-(3-methoxyphenyl)-1-(5-methyl-1-triphenylmethyl-1-H-imidazol-4-yl)-1-butanol obtained is recrystallized from ethyl acetate.
Yield: 7%
M.Pt.: 155° C.
Analysis for $C_{34}H_{34}N_2O_2$ in %:

| Calculated: | C | 81.24 | H | 6.82 | N | 5.57 |
|---|---|---|---|---|---|---|
| Found: | | 80.95 | | 6.84 | | 5.39 |

1.3.j 4-(2-chloro-5-methoxyphenyl)-1-(1-triphenylmethyl-1H-imidazol-4-yl)-1-butanol.

This compound is obtained from the starting compounds prepared in Examples 1.1.j and 1.2.a. The product is used as such in the following step (Example 1.4.j).
Yield: 57%

1.4 Cyclization of the 4-phenyl-1-(1-triphenylmethyl-1H-imidazol-4-yl)-1-butanols of formula II.

This cyclization is performed according to the following procedure: 1 g of a 4-phenyl-1-(1-triphenylmethyl-1H-imidazol-4-yl)-1-butanol prepared in Example 1.3 is dissolved at room temperature in 10 ml of 99% formic acid. The reaction mixture is heated to reflux temperature for 1 to 12 hours whilst the progress of the reaction is followed by reverse-phase HPLC chromatography. When the reaction is considered to be over, the formic acid is distilled off under reduced pressure and the distillation residue is taken up in a toluene-water mixture. The aqueous phase is decanted and washed with an equal volume of toluene. The aqueous phase is brought to pH 9 by addition of an aqueous solution of sodium hydroxide and is extracted with dichloromethane or ethyl acetate. The organic phase is dried over sodium sulfate and the solvent is evaporated under reduced pressure. An oil is obtained which is purified by preparative HPLC chromatography.

1.4a 4-(1,2,3,4-tetrahydro-5-methyl-1-naphthalenyl)-1H-imidazole.

This compound is obtained from the compound prepared in Example 1.3.a.

The reaction mixture is kept at reflux temperature for 8 hours. Preparative chromatography is carried out under the following conditions: stationary phase: silica; eluent: mixture of 97.5: 2.5: 0.25 (v/v/v) dichloromethane-methanol-ammonia in a 12 mole/l aqueous solution. The 4-(1,2,3,4-tetrahydro-5-methyl-1-naphthalenyl)-1H-imidazole finally obtained is recrystallized from ethyl acetate.

Yield: 79.4%
M.Pt.: 134.9° C.
Analysis for $C_{14}H_{16}N_2$ in %:

| | | | | | | | |
|---|---|---|---|---|---|---|---|
| Calculated: | C | 79.2 | H | 7.6 | N | 13.2 | |
| Found: | | 79.15 | | 7.85 | | 13.55 | |

1.4.b 4-(1,2,3,4-tetrahydro-6-methyl-1-naphthalenyl)-1H-imidazole and 4-(1,2,3,4-tetrahydro-8-methyl-1-naphthalenyl)-1H-imidazole.

These two isomers are obtained from the compound prepared in Example 1.3.b. The reaction mixture is kept at reflux temperature for 1 hour. Preparative chromatography is carried out under the following conditions: stationary phase: silica; eluent: 95:5:0.5 (v/v/v) mixture of dichloromethane-2-propanol-ammonia in a 12 mole/l aqueous solution. The 4-(1,2,3,4-tetrahydro-6-methyl-1-naphthalenyl)-1H-imidazole is recrystallized from ethyl acetate.

Yield: 8%
M.Pt.: 138.8° C.
Analysis for $C_{14}H_{16}N_2$ in %:

| | | | | | | | |
|---|---|---|---|---|---|---|---|
| Calculated: | C | 79.2 | H | 7.6 | N | 13.19 | |
| Found: | | 79.14 | | 7.99 | | 13.22 | | and the 4-(1,2,3,4-tetrahydro-8-methyl-1-naphthalenyl)-1H-imidazole is recrystallized from a mixture of ethyl acetate-diethyl ether.

M.Pt.: 162° C.
Analysis for $C_{14}H_{16}N_2$ in %:

| | | | | | | | |
|---|---|---|---|---|---|---|---|
| Calculated: | C | 79.2 | H | 7.6 | N | 13.19 | |
| Found: | | 79.48 | | 7.98 | | 13.42 | |

1.4.c 4-(6-chloro-1,2,3,4-tetrahydro-1-naphthalenyl)-1H-imidazole and 4-(8-chloro-1,2,3,4-tetrahydro-1-naphthalenyl)-1H-imidazole.

These two isomers are obtained from the compound prepared in Example 1.3.c. The reaction mixture is kept at reflux temperature for 12 hours. Preparative chromatography is carried out under the following conditions: stationary phase: silica; eluent: 90:10:5 (v/v/v) mixture of ethyl acetate-hexane-ammonia in a 12 mole/l aqueous solution diluted to 10% with ethanol. The products obtained are recrystallized from ethyl acetate. 4-(6-chloro-1,2,3,4-tetrahydro-1-naphthalenyl)-1H-imidazole M.Pt.: 151.7° C.
Analysis for $C_{13}H_{13}ClN_2$ in %:

| | | | | | | | |
|---|---|---|---|---|---|---|---|
| Calculated: | C | 67.1 | H | 5.63 | N | 12.04 | |
| Found: | | 67.0 | | 5.7 | | 12.59 | | and 4-(8-chloro-1,2,3,4-tetrahydro-1-naphthalenyl)-1H-imidazole
M.Pt.: 182.9° C.

Analysis for $C_{13}H_{13}ClN_2$ in %

| | | | | | | | |
|---|---|---|---|---|---|---|---|
| Calculated: | C | 67.1 | H | 5.63 | N | 12.04 | |
| Found: | | 67.04 | | 5.68 | | 12.26 | |

1.4.d 4-(1,2,3,4-tetrahydro-6-(1-methylethoxy)-1-naphthalenyl)-1H-imidazole and 4-(1,2,3,4-tetrahydro-8-(1-methylethoxy)-1-naphthalenyl)-1H-imidazole.

These two isomers are obtained from the compound prepared in Example 1.3.d. The reaction mixture is kept at reflux temperature for 6 hours. Preparative chromatography is carried out under the following conditions: stationary phase: silica; eluent: 96:4:0.5 (v/v/v) mixture of dichloromethane-ethanol-ammonia in a 12 mole/l aqueous solution. The products obtained are recrystallized from an ethyl acetate-diethyl ether mixture.

4-(1,2,3,4-tetrahydro-6-(1-methylethoxy)-1-naphthalenyl)-1H-imidazole
Yield:13%
M.Pt. :111.9° C.
Analysis for $C_{16}H_{20}N_2O$ in %:

| | | | | | | | |
|---|---|---|---|---|---|---|---|
| Calculated: | C | 74.96 | H | 7.9 | N | 10.93 | |
| Found: | | 74.75 | | 8.14 | | 10.85 | | and 4-(1,2,3,4-tetrahydro-8-(1-methylethoxy)-1-naphthalenyl)-1H-imidazole.
M.Pt.: 133.5° C.
Analysis for $C_{16}H_{20}N_2O$ in %:

| | | | | | | | |
|---|---|---|---|---|---|---|---|
| Calculated: | C | 74.96 | H | 7.9 | N | 10.93 | |
| Found: | | 74.93 | | 8.14 | | 10.91 | |

1.4.e 4-(1,2,3,4-tetrahydro-5,6-dimethoxy-1-naphthalenyl)-1H-imidazole.

This compound is obtained from the compound prepared in Example 1.3.e. The reaction mixture is kept at reflux temperature for 3 hours. The 4-(1,2,3,4-tetrahydro-5,6-dimethoxy-1-naphthalenyl)-1H-imidazole is isolated by crystallization from ethyl acetate.

Yield: 60%
M.Pt.: 160° C.
Analysis for $C_{15}H_{18}N_2O_2$ in %:

| | | | | | | | |
|---|---|---|---|---|---|---|---|
| Calculated: | C | 69.76 | H | 6.97 | N | 10.85 | |
| Found: | | 70.00 | | 7.03 | | 10.77 | |

1.4.f 4-(1,2,3,4-tetrahydro-6,7-dimethoxy-1-naphthalenyl)-1H-imidazole.

This compound is obtained from the compound prepared in Example 1.3.f. The reaction mixture is kept at reflux temperature for 3 hours. The 4-(1,2,3,4-tetrahydro-6,7-dimethoxy-1-naphthalenyl)-1H-imidazole is isolated by crystallization from ethyl acetate.

Yield: 73%
M.Pt.: 140° C.
Analysis for $C_{15}H_{18}N_2O_2$ in %:

| | | | | | | | |
|---|---|---|---|---|---|---|---|
| Calculated: | C | 69.76 | H | 6.97 | N | 10.85 | |
| Found: | | 69.30 | | 7.41 | | 10.50 | |

1.4.g 4-(1,2,3,4-tetrahydro-6-methoxy-1-naphthalenyl)-1H-imidazole and 4-(1,2,3,4-tetrahydro-8-methoxy-1-naphthalenyl)-1H-imidazole.

These two isomers are obtained from the compound prepared in Example 1.3.g. The reaction mixture is kept at reflux temperature for 3 hours. Preparative chromatography is carried out under the following conditions: stationary phase: silica; eluent: 97.5:2.5 (v/v) mixture of dichloromethane-methanol.

The 4-(1,2,3,4-tetrahydro-6-methoxy-1-naphthalenyl)-1H-imidazole is recrystallized from ethyl acetate
Yield: 33%
M.Pt.: 160°–165° C.
Analysis for $C_{14}H_{16}N_2O$ in %:

| Calculated: | C | 73.65 | H | 7.06 | N | 12.27 |
|---|---|---|---|---|---|---|
| Found: | | 73.70 | | 7.05 | | 12.27 | and the 4-(1,2,3,4-tetrahydro-8-methoxy-1-naphthalenyl)-1H-imidazole is recrystallized from diethyl ether.
Yield: 46%
M.Pt.: 135°–140° C.
Analysis for $C_{14}H_{16}N_2O$ in %:

| Calculated: | C | 73.65 | H | 7.06 | N | 12.27 |
|---|---|---|---|---|---|---|
| Found: | | 73.30 | | 7.12 | | 12.27 |

1.4.h 4-(1,2,3,4-tetrahydro-5-methoxy-1-naphthalenyl)-1H-imidazole.

This compound is obtained from the compound prepared in Example 1.3.h. The reaction mixture is kept at reflux temperature for 2 hours. Preparative chromatography is carried out under the following: conditions: stationary phase: silica; eluent: 95:5 (v/v) mixture of dichloromethane-methanol. The 4-(1,2,3,4-tetrahydro-5-methoxy-1-naphthalenyl)-1H-imidazole obtained is recrystallized from toluene.
Yield: 20%
M.Pt.: 156° C.
Analysis for $C_{14}H_{16}N_2O$ in %:

| Calculated: | C | 73.65 | H | 7.06 | N | 12.27 |
|---|---|---|---|---|---|---|
| Found: | | 73.43 | | 7.09 | | 12.10 |

1.4.i 5-methyl-4-(1,2,3,4-tetrahydro-6-methoxy-1-naphthalenyl)-1H-imidazole and 5-methyl-4-(1,2,3,4-tetrahydro-8-methoxy-1-naphthalenyl)-1H-imidazole.

These two isomers are obtained from the compound prepared in Example 1.3.i. The reaction mixture is kept at reflux temperature for 2 hours. Preparative chromatography is carried out under the following conditions: stationary phase: silica; eluent: 97:3 (v/v) mixture of dichloromethane-methanol.

The 5-methyl-4-(1,2,3,4-tetrahydro-6-methoxy-1-naphthalenyl)-1H-imidazole is recrystallized from 2-propanol
M.Pt.: 216° C.
Analysis for $C_{15}H_{18}N_2O$ in %:

| Calculated: | C | 74.34 | H | 7.49 | N | 11.56 |
|---|---|---|---|---|---|---|
| Found: | | 74.01 | | 7.58 | | 11.22 | and the 5-methyl-4-(1,2,3,4-tetrahydro-8-methoxy-1-naphthalenyl)-1H-imidazole is recrystallized from a mixture of 2-propanol-di(1-methylethyl)ether.
M.Pt.: 135° C.

Analysis for $C_{15}H_{18}N_2O$ in %:

| Calculated: | C | 74.34 | H | 7.49 | N | 11.56 |
|---|---|---|---|---|---|---|
| Found: | | 73.61 | | 7.70 | | 11.36 |

1.4.j 4-(5-chloro-1,2,3,4-tetrahydro-8-methoxy-1-naphthalenyl)-1H-imidazole.

This compound is obtained from the compound prepared in Example 1.3.j. The reaction mixture is kept at reflux temperature for 3 hours. The 4-(5-chloro-1,2,3,4-tetrahydro-8-methoxy-1-naphthalenyl)-1H-imidazole is extracted from the reaction medium with chloroform and recrystallized from this solvent.
Yield: 81%
M.Pt.: 204° C.
Analysis for $C_{14}H_{15}ClN_2O$ in %:

| Calculated: | C | 64.0 | H | 5.75 | N | 10.66 |
|---|---|---|---|---|---|---|
| Found: | | 63.82 | | 5.82 | | 10.53 |

1.5 Preparation of optically active 4-(1,2,3,4-tetrahydro-1-naphthalenyl)-1H-imidazoles.

(+)-4-(1,2,3,4-tetrahydro-6-methoxy-1-naphthalenyl)-1H-imidazole and (−)-4-(1,2,3,4-tetrahydro-6-methoxy-1-naphthalenyl)-1H-imidazole.

The racemic 4-(1,2,3,4-tetrahydro-6-methoxy-1-naphthalenyl)-1H-imidazole prepared in Example 1.4.g is resolved by chromatography on a chiral support (CHIRACEL OJ from the DAICEL Company: cellulose paramethylbenzoate) with an 80:20:0.1 (v/v/v) mixture of hexane-2-propanoldiethylamine as eluent. The (+)-4-(1,2,3,4-tetrahydro-6-methoxy-1-naphthalenyl)-1H-imidazole is eluted first:

Yield after recrystallization from ethyl acetate: 66%
M.Pt.: 183° C.
$[\alpha]_D^{25}$:+13.85° (c=1, methanol)

The (−)-4-(1,2,3,4-tetrahydro-6-methoxy-1-naphthalenyl)-1H-imidazole is eluted next:

Yield after recrystallization from ethyl acetate: 62%
M.Pt.: 183° C.
$[\alpha]_D^{25}$:−14.0° (c=1, methanol)

EXAMPLE 2

Preparation of the 4-(2,3-dihydro-1H-inden-1-yl)-1H-imidazoles of formula I (n=1, $R_1$, $R_2$, $R_3$ and $R_4$=H, halogen or an alkyl or alkoxy radical with $C_1$–$C_4$ and $R_5$=H or an alkyl radical with $C_1$–$C_4$).

2.1 Preparation of the starting 1-(1-triphenylmethyl-1H-imidazol-4-yl)-1-ethanones of formula VIII.

1-(1-triphenylmethyl-1H-imidazol-4-yl)-1-ethanone.

This compound is prepared according to the method described in U.S. Pat. No. 4,814,343, Example 1.B.4.

2.2 Preparation of 3-phenyl-1-(1-triphenylmethyl-1H-imidazol-4-yl)-2-propen-1-ones of formula IX.

2.2.a 3-(2,3-dimethoxyphenyl)-1-(1-triphenylmethyl-1H-imidazol-4-yl)-2-propen-1-one.

0.149 mole of 2,3-dimethoxybenzaldehyde is added over 5 hours at room temperature to a solution of 0.149 mole of 1-(1-triphenylmethyl-1H-imidazol-4-yl)-1-ethanone prepared in Example 2.1 in a mixture of 800 ml of ethanol and 186 ml of a 2N aqueous solution of sodium hydroxide. The reaction medium is then brought to pH 7.5 by addition of a 5N aqueous solution of hydrochloric acid. The ethanol is distilled off and a solid is formed, which precipitates. This solid is filtered off and washed with water before drying. The solid is redissolved in 2 liters of boiling 2-propanol and the insoluble salts are filtered off. Half the 2-propanol is evaporated off and the 3-(2,3-dimethoxyphenyl)-1-(1-triphenylmethyl-1H-imidazol-4-yl)-2-propen-1-one is recrystallized.

Yield: 75%
M.Pt.: 175°–186° C.
Analysis for $C_{33}H_{28}N_2O_3$ in %:

| | C | H | N |
|---|---|---|---|
| Calculated: | 79.2 | 5.60 | 5.6 |
| Found: | 78.25 | 5.70 | 5.37 |

2.2.b 3-(3-methoxyphenyl)-1-(1-triphenylmethyl-1H-imidazol-4-yl)-2-propen-1-one.

This compound is prepared according to the method described in Example 2.2.a starting from 3-methoxybenzaldehyde.

Yield: 98%
M.Pt.: 173°–175° C.
Analysis for $C_{32}H_{26}N_2O_2$ in %:

| | C | H | N |
|---|---|---|---|
| Calculated: | 81.68 | 5.56 | 5.95 |
| Found: | 81.65 | 5.62 | 5.99 |

2.3 Preparation of the 3-phenyl-1-(1-triphenylmethyl-1H-imidazol-4-yl)-1-propanones of formula X.

2.3.a 3-(2,3-dimethoxyphenyl)-1-(1-triphenylmethyl-1H-imidazol-4-yl)-1-propanone.

0.108 mole of 3-(2,3-dimethoxyphenyl)-1-(1-triphenylmethyl-1H-imidazol-4-yl)-2-propen-1-one prepared in Example 2.2.a in 800 ml of acetic acid is hydrogenated under a hydrogen pressure of 4 kg and in the presence of 3 g of platinum oxide at 20° C. At the end of the reaction, the catalyst is filtered off and the acetic acid is evaporated under reduced pressure.

The residue is purified by chromatography (support:silica; eluent: 99:1:0.1 (v/v/v) mixture of dichloromethane-methanol-ammonia in a 12 mole/l aqueous solution). The 3-(2,3-dimethoxyphenyl)-1-(1-triphenylmethyl-1H-imidazol-4-yl)-1-propanone is isolated first and is used as such in the following step (Example 2.4.a), and, by continuing the chromatography (eluent: 95:5:0.5 (v/v/v) mixture of dichloromethane-methanol-ammonia in a 12 mole/l aqueous solution), the 3-(2,3-dimethoxyphenyl)-1-(1H-imidazol-4-yl)-1-propanone is isolated next, which is also used as such in the following step (Example 2.5.a).

2.3.b 3-(3-methoxyphenyl)-1-(1-triphenylmethyl-1H-imidazol-4-yl)-1-propanone.

This compound is obtained according to the procedure described in Example 2.3.a. By chromatography, the 3-(3-methoxyphenyl)-1-(1-triphenylmethyl-1H-imidazol-4-yl)-1-propanone is isolated first and used as such in the following step (Example 2.4.b), and by continuing the chromatography, 3-(3-methoxyphenyl)-1-(1H-imidazol-4-yl)-1-propanone is isolated next, which is crystallized from ethyl acetate before being used in the following step (Example 2.5.b).

2.4 Preparation of the 1-(1H-imidazol-4-yl)-3-phenyl-1-propanones of formula XI.

2.4.a 3-(2,3-dimethoxyphenyl)-1-(1H-imidazol-4-yl)-1-propanone.

17.88 g (0.0687 mole) of 3-(2,3-dimethoxyphenyl)-1-(1-triphenylmethyl-1H-imidazol-4-yl)-1-propanone prepared in Example 2.3.a are heated in 100 ml of formic acid for half an hour at 80° C. The reaction medium is then cooled to room temperature and the triphenylmethanol which has precipitated during cooling is filtered off. Formic acid is distilled off and the residue is taken up in water. The aqueous phase is then brought to pH 9 by addition of a 12 mole/l aqueous solution of ammonia. The precipitate which has formed is filtered off and dried and 8.35 g of 3-(2,3-dimethoxyphenyl)-1-(1H-imidazol-4-yl)-1-propanone are obtained.

Yield: 90%
M.Pt.: 120°–125° C.
Analysis for $C_{14}H_{16}N_2O_3$ in %:

| | C | H | N |
|---|---|---|---|
| Calculated: | 64.6 | 6.2 | 10.76 |
| Found: | 64.04 | 6.21 | 10.33 |

2.4.b 3-(3-methoxyphenyl)-1-(1H-imidazol-4-yl)-1-propanone.

Using the same procedure as in Example 2.4.a and starting with 10.28 g (0.0217 mole) of 3-(3-methoxyphenyl)-1-(1-triphenylmethyl-1H-imidazol-4-yl)-1-propanone prepared in Example 2.3.b, 3.68 g of 3-(3-methoxyphenyl-1-(1H-imidazol-4-yl)-1-propanone are obtained after crystallization from ethyl acetate.

Yield: 73%
M.Pt.: 127°–129° C.
Analysis for $C_{13}H_{14}N_2O_2$ in %:

| | C | H | N |
|---|---|---|---|
| Calculated: | 67.82 | 6.08 | 12.17 |
| Found: | 67.18 | 6.10 | 11.70 |

2.5 Preparation of the 4-(1H-inden-3-yl)-1H-imidazoles of formula III.

2.5.a 4-(6,7-dimethoxy-1H-inden-3-yl)-1H-imidazole. 5 g (0.0206 mole) of 3-(2,3-dimethoxyphenyl)-1-(1H-imidazol-4-yl)-1-propanone prepared in Example 2.4.a (and/or in Example 2.3.a) are stirred at room temperature for 16 hours in 100 ml of a 50:50 (v/v) mixture of 85% phosphoric acid and 95% sulphuric acid. The reaction medium is then poured onto ice, the mixture is brought to pH 7.5 by addition of an aqueous solution of sodium hydroxide cooled to a temperature of less than 10° C., and the mixture is then extracted with dichloromethane. The solvent is evaporated from the organic phase and the residue is treated by chromatography (stationary phase:silica; eluent: 95:5 (v/v) mixture of dichloromethane-methanol). 2.3 g of 4-(6,7-dimethoxy-1H-inden-3-yl)-1H-imidazole are obtained.

Yield: 41%
M. Pt.: 150° C.

2.5.b 4-(6-methoxy-1H-inden-3-yl)-1H-imidazole.

Using the same method as in Example 2.5.a and starting with 12.93 g (0.0562 mole) of 3-(3-methoxyphenyl)-1-(1H-imidazol-4-yl)-1-propanone prepared in Example 2.4.b (and/or in Example 2.3.b), 3.76 g of 4-(6-methoxy-1H-inden-3-yl)-1H-imidazole are obtained after crystallization from acetonitrile.

Yield: 31.5%
M.Pt.: 170° C.
Analysis for $C_{13}H_{12}N_2O$ in %:

| Calculated: | C | 73.56 | H | 5.70 | N | 13.20 |
|---|---|---|---|---|---|---|
| Found: | | 73.50 | | 5.70 | | 13.23 |

2.6 Hydrogenation of the 4-(1H-inden-3-yl)-1H-imidazoles of formula III.

2.6.a 4-(2,3-dihydro-4,5-dimethoxy-1H-inden-1-yl)-1H-imidazole.

2.3 g (0.0095 mole) of 4-(6,7-dimethoxy-1H-inden-3-yl)-1H-imidazole prepared in Example 2.5.a in 200 ml of methanol are hydrogenated under a hydrogen pressure of 2 kg at 40° C., in the presence of palladium on carbon (Pd 10%). At the end of the reaction, the catalyst is filtered off and the methanol distilled. The residue is crystallized from ethyl acetate and 4-(2,3-dihydro-4,5-dimethoxy-1H-inden-1-yl)-1H-imidazole is obtained.

M.Pt.: 156°–158° C.

Analysis for $C_{14}H_{16}N_2O_2$ in %:

| Calculated: | C | 68.83 | H | 6.60 | N | 11.47 |
|---|---|---|---|---|---|---|
| Found: | | 68.94 | | 6.63 | | 11.34 |

2.6.b 4-(2,3-dihydro-5-methoxy-1H-inden-1-yl)-1H-imidazole.

This compound is prepared according to the method described in Example 2.6.a starting with 4-(6-methoxy-1H-inden-3-yl)-1H-imidazole prepared in Example 2.5.b.

Yield: 81.2%

M.Pt.: 180°–182° C.

Analysis for $C_{13}H_{14}N_2O$ in %:

| Calculated: | C | 72.89 | H | 6.54 | N | 13.08 |
|---|---|---|---|---|---|---|
| Found: | | 73.14 | | 6.58 | | 12.68 |

EXAMPLE 3

Preparation of the 5,6,7,8-tetrahydro-5-(1H-imidazol-4-yl)-naphthalenols and of the 2,3-dihydro-1-(1H-imidazol-4-yl)-1H-indenols of formula I (n=1 or 2; $R_1$, $R_2$, $R_3$ and/or $R_4$=OH; and $R_5$=H or alkyl with $C_1$–$C_4$).

These compounds are prepared according to the following procedure: 1 g of a 4-(1,2,3,4-tetrahydro-1-naphthalenyl)-1H-imidazole or of a 4-(2,3-dihydro-1H-inden-1-yl)-1H-imidazole carrying at least one alkoxy radical having 1 to 4 carbon atoms, is heated for half an hour in 20 ml of azeotropic hydrobromic acid at the boiling point. The hydrobromic acid is then distilled off under reduced pressure and the residue is taken up in water and brought to pH 10 by the addition of an aqueous solution of sodium hydroxide. The water is distilled off under reduced pressure and the residue is extracted with 2-propanol at the boiling point. The insoluble salts are filtered off and the solvent is partially evaporated until crystals appear. If these compounds can not be isolated in this way, the corresponding hydrochloride is formed according to the following procedure: gaseous hydrochloric acid is dissolved in 2-propanol and the crude compound previously formed is added to this solution. The precipitate which has formed is filtered off and is purified by recrystallization if necessary.

3.a (+)-5,6,7,8-tetrahydro-5-(1H-imidazol-4-yl)-2-naphthalenol.

Starting from 1.5 g of (+)-4-(1,2,3,4-tetrahydro-6-methoxy-1-naphthalenyl)-1H-imidazole prepared in Example 1.5, 0.7 g of (+)-5,6,7,8-tetrahydro-5-(1H-imidazol-4-yl)-2-naphthalenol are obtained.

M.Pt.: 243°–246° C.

$[\alpha]_D^{25}$: +5.11° (c=1; methanol)

Analysis for $C_{13}H_{14}N_2O$ in %:

| Calculated: | C | 72.87 | H | 6.58 | N | 13.07 |
|---|---|---|---|---|---|---|
| Found: | | 72.23 | | 6.80 | | 12.64 |

3.b (−)-5,6,7,8-tetrahydro-5-(1H-imidazol-4-yl)-2-naphthalenol.

Starting from 1.5 g of (−)-4-(1,2,3,4-tetrahydro-6-methoxy-1-naphthalenyl)-1H-imidazole prepared in Example 1.5, 0.6 g of (−)-5,6,7,8-tetrahydro-5-(1H-imidazol-4-yl)-2-naphthalenol are obtained.

M.Pt.: 243°–246° C.

$[\alpha]_D^{25}$: −5.5° (c=1; methanol)

3.c 5,6,7,8-tetrahydro-5-(1H-imidazol-4-yl)-2,3-napthalenediol hydrochloride.

Starting from 1.5 g of 4-(1,2,3,4-tetrahydro-6,7-dimethoxy-1-naphthalenyl)-1H-imidazole prepared in Example 1.4.f, 0.63 g of 5,6,7,8-tetrahydro-5-(1H-imidazol-4-yl)-2,3-napthalenediol hydrochloride are obtained.

M.Pt.: 238°–242° C.

Analysis for $C_{13}H_{14}N_2O_2 \cdot HCl$ in %:

| Calculated: | C | 58.54 | H | 5.67 | N | 10.50 |
|---|---|---|---|---|---|---|
| Found: | | 57.21 | | 5.73 | | 10.17 |

3.d 5,6,7,8-tetrahydro-5-(1H-imidazol-4-yl)-1,2-napthalenediol hydrochloride.

Starting from 10.18 g of 4-(1,2,3,4-tetrahydro-5,6-dimethoxy-1-naphthalenyl)-1H-imidazole prepared in Example 1.4.e., 6.93 g of 5,6,7,8-tetrahydro-5-(1H-imidazol-4-yl)-1,2-napthalenediol hydrochloride are obtained, after recrystallization from a mixture of 2-propanol-di(1-methylethyl)ether.

Yield: 66%

M.Pt.: 245°–250° C.

Analysis for $C_{13}H_{14}N_2O_2 \cdot HCl$ in %:

| Calculated: | C | 58.53 | H | 5.63 | N | 10.50 | Cl− | 13.32 |
|---|---|---|---|---|---|---|---|---|
| Found: | | 58.47 | | 5.66 | | 10.53 | | 12.86 |

3.e 5,6,7,8-tetrahydro-5-(1H-imidazol-4-yl)-1-napthalenol hydrochloride.

Starting from 1.66 g of 4-(1,2,3,4-tetrahydro-5-methoxy-1-naphthalenyl)-1H-imidazole prepared in Example 1.4.h., 1.28 g of 5,6,7,8-tetrahydro-5-(1H-imidazol-4-yl)-1-napthalenol hydrochloride are obtained, after recrystallization from a mixture of 2-propanol-di(1-methylethyl)ether.

Yield: 85%

M.Pt.: 215°–222° C.

Analysis for $C_{13}H_{14}N_2 \cdot HCl$ in %:

| Calculated: | C | 62.27 | H | 6.03 | N | 11.17 |
|---|---|---|---|---|---|---|
| Found: | | 60.36 | | 6.07 | | 10.39 |

3.f 2,3-dihydro-1-(1H-imidazol-4-yl)-1H-indene-4,5-diol hydrochloride.

Starting from 0.4 g of 4-(2,3-dihydro-4,5-dimethoxy-1H-inden-1-yl)-1H-imidazole prepared in Example 2.6.a, 0.5 g of 2,3-dihydro-1-(1H-imidazol-4-yl)-1H-indene-4,5-diol hydrochloride are obtained.

Yield: 83%
M.Pt.: 240°–245° C.
Analysis for $C_{12}H_{12}N_2O_2 \cdot HCl$ in %:

| | | | | | | |
|---|---|---|---|---|---|---|
| Calculated: | C | 57.04 | H | 5.19 | N | 11.09 |
| Found: | | 56.96 | | 4.84 | | 10.93 |

3.g 2,3-dihydro-1-(1H-imidazol-4-yl)-1H-indene-5-ol hydrochloride.

Starting from 2 g of 4-(2,3-dihydro-5-methoxy-1H-inden-1-yl)-1H-imidazole prepared in Example 2.6.b, 0.36 g of 2,3-dihydro-1-(1H-imidazole-4-yl)-1H-indene-5-ol hydrochloride are obtained.
M.Pt.: 170° C.
Analysis for $C_{12}H_{12}N_2O \cdot HCl$ in %:

| | | | | | | | | |
|---|---|---|---|---|---|---|---|---|
| Calculated: | C | 60.88 | H | 5.53 | N | 11.83 | Cl⁻ | 14.98 |
| Found: | | 60.99 | | 5.60 | | 11.55 | | 14.46 |

We claim:

1. A compound selected from the group consisting of substituted 4-(1,2,3,4-tetrahydro-1-naphthalenyl)-1H-imidazole and substituted 4-(2,3-dihydro-1H-inden-1-yl)-1H-imidazole, the optically active isomers thereof and racemic mixtures thereof, of the formula

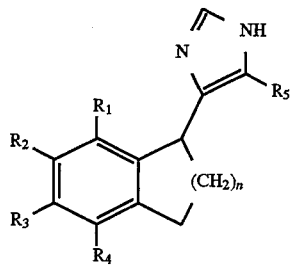

(I)

wherein n=1 or 2, $R_1$, $R_2$, $R_3$ and $R_4$, which may be the same or different, each represent a hydrogen or halogen atom, a hydroxyl group, or an alkyl or alkoxy radical, and $R_5$ represents a hydrogen atom or an alkyl radical, with the proviso that $R_1$, $R_2$, $R_3$, $R_4$ and $R_5$ cannot simultaneously be hydrogen when n is equal to 2, the alkyl and alkoxy radicals having 1 to 4 carbon atoms, or a non-toxic pharmaceutically acceptable acid addition salt thereof.

2. A compound as claimed in claim 1, namely (+)-4-(1,2,3,4-tetrahydro-6-methoxy-1-naphthalenyl)-1H-imidazole or a non-toxic pharmaceutically acceptable acid addition salt thereof.

3. A compound as claimed in claim 1, namely 4-(1,2,3,4-tetrahydro-5-methyl-1-naphthalenyl)-1H-imidazole or a non-toxic pharmaceutically acceptable acid addition salt thereof.

4. A compound as claimed in claim 1, namely 4-(2,3-dihydro-5-methoxy-1H-inden-1-yl)-1H-imidazole or a non-toxic pharmaceutically acceptable acid addition salt thereof.

5. A compound as claimed in claim 1, namely (+)-5,6,7,8-tetrahydro-5-(1H-imidazol-4-yl)-2-naphthalenol or a non-toxic pharmaceutically acceptable acid addition salt thereof.

6. A compound as claimed in claim 1, namely 4-(1,2,3,4-tetrahydro-5-methoxy-1-naphthalenyl)-1H-imidazole or a non-toxic pharmaceutically acceptable acid addition salt thereof.

7. A compound as claimed in claim 1, namely 5,6,7,8-tetrahydro-5-(1H-imidazol-4-yl)-1-naphthalenol or a non-toxic pharmaceutically acceptable acid addition salt thereof.

8. A compound as claimed in claim 1, namely 4-(1,2,3,4-tetrahydro-6-methoxy-1-naphthalenyl)-1H-imidazole or a non-toxic pharmaceutically acceptable acid addition salt thereof.

9. A compound as claimed in claim 1, namely 2,3-dihydro-1-(1H-imidazol-4-yl)-1H-indene-5-ol or a non-toxic pharmaceutically acceptable acid addition salt thereof.

10. A compound as claimed in claim 1, namely 4-(1,2,3,4-tetrahydro-8-methoxy-1-naphthalenyl)-1H-imidazole or a non-toxic pharmaceutically acceptable acid addition salt thereof.

11. A compound as claimed in claim 1, namely 4-(1,2,3,4-tetrahydro-6,7-dimethoxy-1-naphthalenyl)-1H-imidazole or a non-toxic pharmaceutically acceptable acid addition salt thereof.

12. A compound as claimed in claim 1, namely 5,6,7,8-tetrahydro-5-(1H-imidazol-4-yl)-2,3-naphthalenediol or a non-toxic pharmaceutically acceptable acid addition salt thereof.

13. A pharmaceutical composition comprising a therapeutically effective amount of a substituted 1H-imidazole as claimed in claim 1 and a pharmaceutically acceptable solid or liquid diluent or carrier therefor.

* * * * *